United States Patent
Sukegawa

(10) Patent No.: US 9,310,278 B2
(45) Date of Patent: Apr. 12, 2016

(54) APPEARANCE INSPECTION APPARATUS AND APPEARANCE INSPECTION METHOD WITH UNEVENESS DETECTING

(71) Applicant: BRIDGESTONE CORPORATION, Tokyo (JP)

(72) Inventor: Tetsuya Sukegawa, Kodaira (JP)

(73) Assignee: BRIDGESTONE CORPORATION, Tokyo (JP)

( * ) Notice: Subject to any disclaimer, the term of this patent is extended or adjusted under 35 U.S.C. 154(b) by 4 days.

(21) Appl. No.: 14/365,668

(22) PCT Filed: Dec. 28, 2012

(86) PCT No.: PCT/JP2012/084058
§ 371 (c)(1),
(2) Date: Jun. 16, 2014

(87) PCT Pub. No.: WO2013/100124
PCT Pub. Date: Jul. 4, 2013

(65) Prior Publication Data
US 2015/0002847 A1  Jan. 1, 2015

(30) Foreign Application Priority Data
Dec. 28, 2011 (JP) ................................ 2011-288373

(51) Int. Cl.
*G01M 17/02* (2006.01)
*G01N 21/95* (2006.01)
(Continued)

(52) U.S. Cl.
CPC ............. *G01M 17/027* (2013.01); *G01B 11/24* (2013.01); *G01B 11/25* (2013.01);
(Continued)

(58) Field of Classification Search
CPC . G01M 17/027; G01B 11/306; G01B 11/303; G01B 11/952; G01B 11/30; G01N 21/95; G01N 21/57; G01N 2021/575; G01N 21/25; G01N 21/251; G01N 21/255; G01N 21/27; G01N 21/29; G01N 21/55; G01N 2021/8841; G01N 2021/8851; G01N 2021/887; G01N 2021/8887
See application file for complete search history.

(56) References Cited

U.S. PATENT DOCUMENTS 6,124,925 A * 9/2000 Kaneko et al. ............. 356/237.1
7,177,740 B1 * 2/2007 Guangjun et al. ............... 73/146
(Continued)

FOREIGN PATENT DOCUMENTS

EP  0 898 163 A1  2/1999
EP  0 955 538 A1  11/1999
(Continued)

OTHER PUBLICATIONS
International Search Report issued in International Patent Application No. PCT/JP2012/084058 dated Feb. 5, 2013.
(Continued)

*Primary Examiner* — Michael P Lapage
(74) *Attorney, Agent, or Firm* — Oliff PLC

(57) ABSTRACT

An appearance inspection apparatus and an appearance inspection method for detecting a shape, surface unevenness, shine or changes in tone on the surface. The method includes steps of acquiring reflected luminance data on the sample surface by casting a slit light having an intermediate wavelength of three types of lights having different wavelengths, receiving reflected light of the slit light, acquiring surface data by casting two lights of different wavelengths other than the intermediate wavelength at a position other than the position illuminated by the slit light on the sample surface from two different directions so as to overlap two lights with each other and receiving reflected light, detecting surface unevenness from a ratio between the intensities of lights, changes in tone by combining reflected luminance data and surface data, gloss on the sample surface based on the presence or absence of surface unevenness and the changes in color tone.

5 Claims, 7 Drawing Sheets

(51) Int. Cl.
*G01N 21/952* (2006.01)
*G01B 11/24* (2006.01)
*G01N 21/25* (2006.01)
*G01N 21/57* (2006.01)
*G01B 11/25* (2006.01)

(52) U.S. Cl.
CPC ......... *G01B 11/2509* (2013.01); *G01N 21/255* (2013.01); *G01N 21/57* (2013.01); *G01N 21/952* (2013.01); *G01N 21/9515* (2013.01)

(56) References Cited

U.S. PATENT DOCUMENTS

| | | | |
|---|---|---|---|
| 2005/0058333 A1* | 3/2005 | Kaneko et al. | 382/141 |
| 2007/0153285 A1* | 7/2007 | Elton et al. | 356/446 |
| 2009/0015823 A1 | 1/2009 | Yoshikawa et al. | |
| 2010/0002244 A1* | 1/2010 | Iino et al. | 356/601 |
| 2010/0063750 A1 | 3/2010 | Floeder et al. | |
| 2011/0188731 A1* | 8/2011 | Sekiguchi | 382/141 |

FOREIGN PATENT DOCUMENTS

| | | |
|---|---|---|
| EP | 1 114 993 A2 | 7/2001 |
| EP | 1 120 640 A1 | 8/2001 |
| EP | 2 078 955 A1 | 7/2009 |
| EP | 2 322 899 A1 | 5/2011 |
| JP | A-58-92904 | 6/1983 |
| JP | A-59-52735 | 3/1984 |
| JP | A-2009-216485 | 9/2009 |
| JP | A-2011-247639 | 12/2011 |
| WO | WO 2010/024254 A1 | 4/2010 |
| WO | 2010/131698 A1 | 11/2010 |

OTHER PUBLICATIONS

International Preliminary Report on Patentability issued in International Patent Application No. PCT/JP2012/084058 dated Feb. 5, 2013.

Jul. 9, 2015 Search Report issued in European Patent Application No. 12863785.7.

* cited by examiner

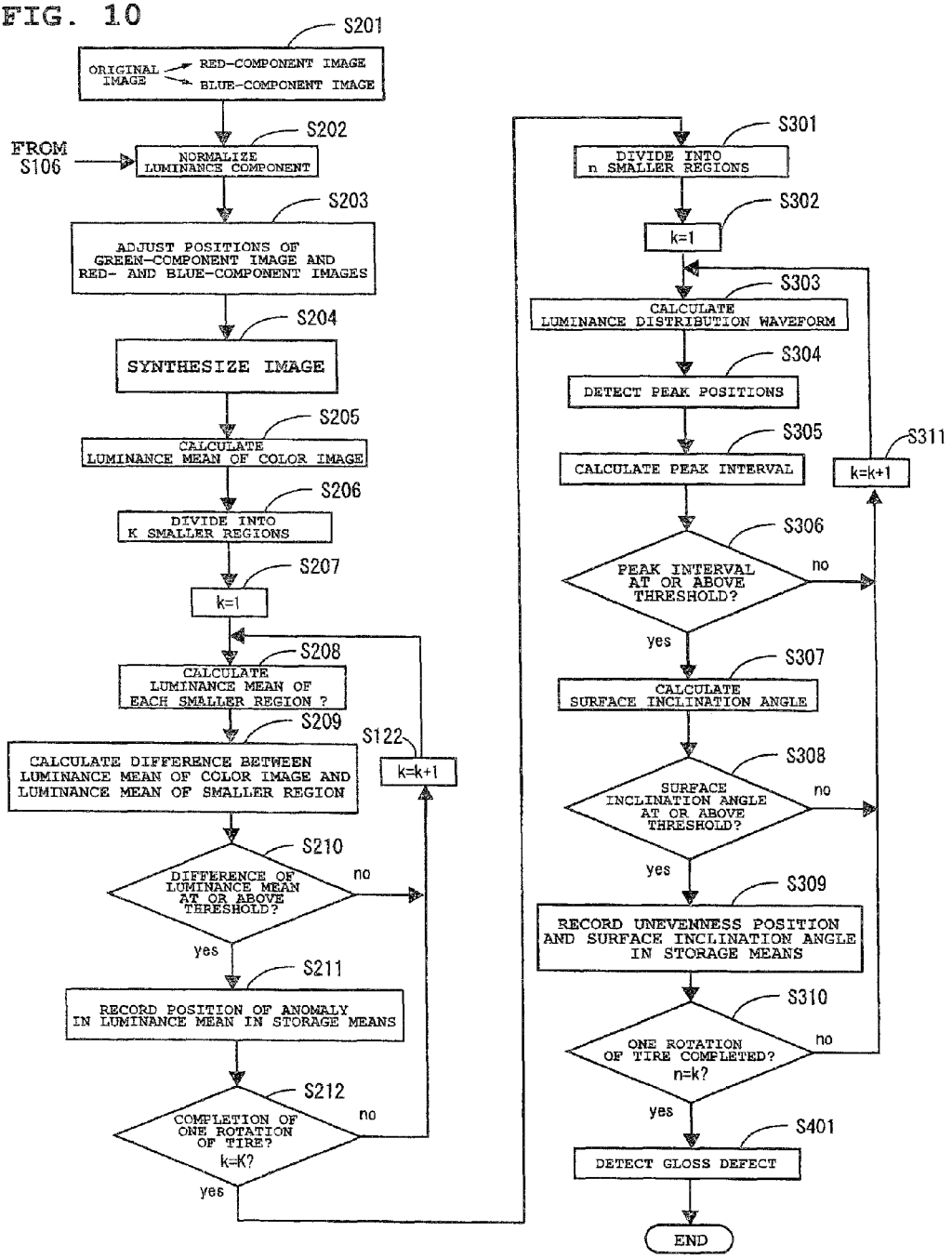

APPEARANCE INSPECTION APPARATUS AND APPEARANCE INSPECTION METHOD WITH UNEVENESS DETECTING

BACKGROUND OF THE INVENTION

1. Field of the Invention

The present invention relates to an appearance inspection apparatus and an appearance inspection method and, in particular, to an appearance inspection apparatus and an appearance inspection method for detecting the shape, surface unevenness, and changes in color tone of a sample under inspection, such as a tire or a tire component.

2. Description of the Related Art

Tire appearance inspections conducted conventionally are shape inspections and surface condition inspections of tires. In a shape inspection, a monochromatic slit light is cast in a radial direction on the surface of a rotating tire and the portion illuminated by the slit light is captured by an area camera. By doing so, sectional images for one rotation of a tire are acquired. Then the thus acquired sectional images are subjected to an image processing and compared with a master image to determine whether there is any shape anomaly or not. Also, in a surface condition inspection, attempts are made to detect minute surface unevenness that cannot be detected in a shape inspection. To do so, red illumination and blue illumination having different wavelengths from each other are directed to the surface of a rotating tire from different directions so as to overlap the cast lights with each other. Then the surface images for one rotation of the tire are acquired by capturing the portion illuminated by the overlapped lights by a line camera all along the circumference of the tire. Then the red component and the blue component contained in the surface images are separated from each other, and the presence or absence of unevenness of the tire surface is determined from the ratio between the intensities of the red component and the blue component. Also, the inclination angles of the tire surface are calculated based on the intensities of the red component and the blue component, and the surface condition is inspected by evaluating the agreement between the changes in the inclination angle distribution and the defect characteristics (e.g., a decision on no anomaly when the inclination angle is at or below a threshold and on surface unevenness anomaly when it is greater than the threshold).

PRIOR ART DOCUMENT

Patent Document

Patent Document 1: WO2010/024254 A1

SUMMARY OF THE INVENTION

Problem to be Solved by the Invention

In a surface condition inspection as described above, however, the presence of surface unevenness is determined from a ratio between the intensities of the red component and the blue component contained in the surface images. As a result, there may be cases where surface conditions other than unevenness are detected as surface unevenness on account of "shine" or "change in color tone", for instance. These irregularities in the ratio between the intensities of the red component and the blue component are considered attributable to the mirror reflection of "shine" of the mold release agent having adhered to the tire surface during molding or the defect of "change in color tone" of the rubber having occurred during molding. To avoid such detection errors, it may be considered necessary to detect the "shine" or "change in color tone" through some image processing. Nevertheless, since the surface images have only red and blue of the three primary colors, there may be cases where the "shine" or "change in color tone" cannot be detected as they are if they contain a green component.

As a solution to the aforementioned problems, the present invention provides an appearance inspection apparatus and an appearance inspection method that can detect not only the shape and minute surface unevenness of a sample under inspection, but also such surface conditions as "shine" or "change in color tone" in shape and surface condition inspections of the appearance inspection.

Means for Solving the Problem

In solving the above-described problems, an appearance inspection apparatus includes a first illuminating means for casting a slit light having an intermediate wavelength, of three types of lights having different wavelengths from each other, on a surface of a sample under inspection, a first imaging means for acquiring reflected luminance data on the surface of the sample by receiving reflected light of the slit light, a second illuminating means for casting two lights of different wavelengths other than the intermediate wavelength on a position other than the position illuminated by the slit light on the sample surface from two different directions so as to overlap the two lights with each other, a second imaging means for acquiring surface data on the sample surface by receiving reflected light from the position where the two lights are overlapped with each other, an unevenness defect detecting means for detecting the presence or absence of surface unevenness from a ratio between intensities of the two lights contained in the surface data, an extraneous color defect detecting means for detecting changes in color tone on the sample surface by synthesizing the reflected luminance data and the surface data, and a gloss defect detecting means for detecting gloss on the sample surface based on the presence or absence of surface unevenness and the changes in color tone.

It is to be understood that the foregoing summary of the invention does not necessarily recite all the features essential to the invention, and subcombinations of all these features are intended to be included in the invention.

BRIEF DESCRIPTION OF THE DRAWINGS

FIG. 10 is a flowchart showing a processing by an inspection processing unit.

BEST MODE FOR CARRYING OUT THE INVENTION

The invention will now be described in detail based on preferred embodiments which do not intend to limit the scope of the claims of the present invention but exemplify the invention. All of the features and the combinations thereof described in the embodiments are not necessarily essential to the invention.

Figure 1:
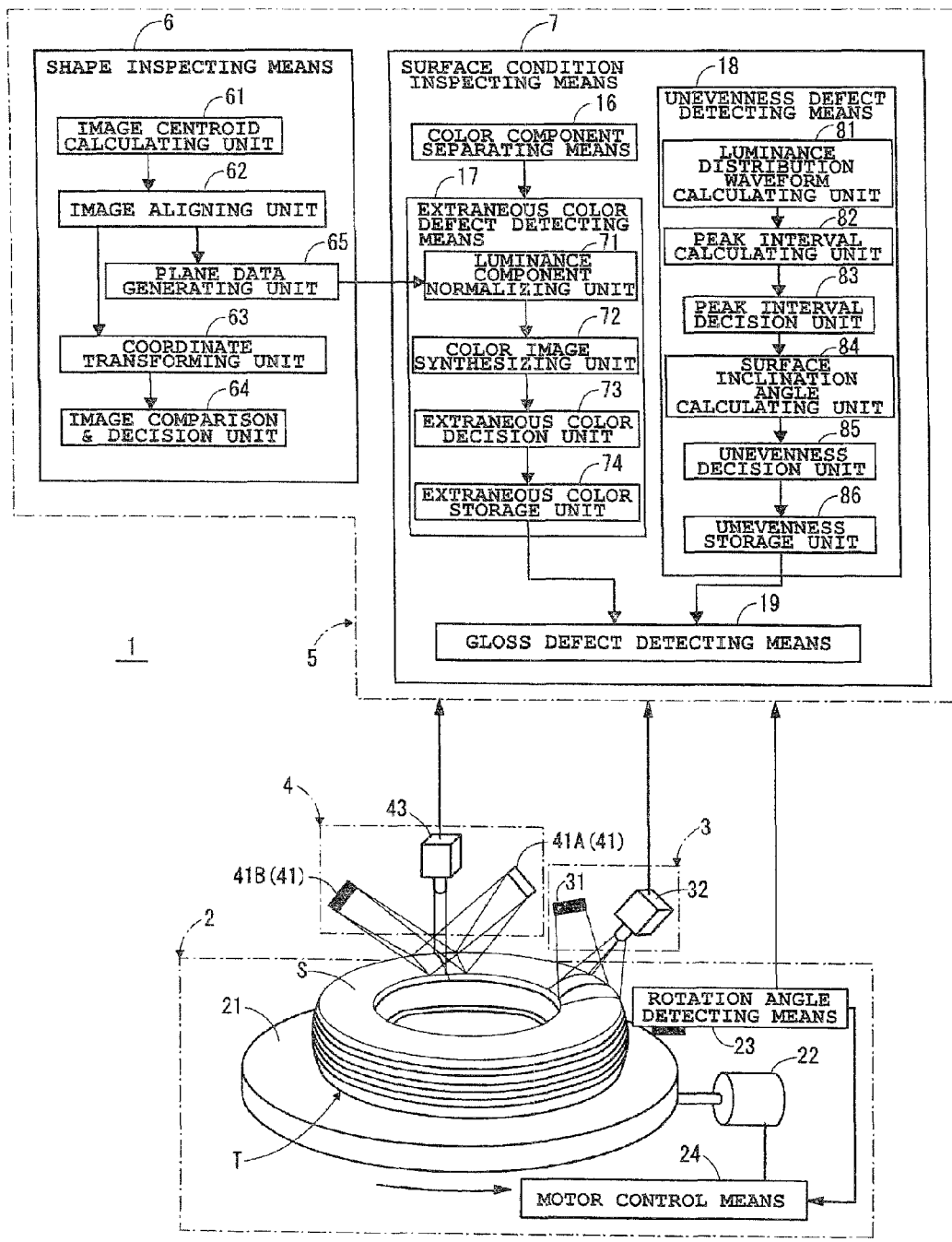
FIG. 1 is a schematic configuration diagram of an appearance inspection apparatus.

FIG. 1 is a configuration diagram of an appearance inspection apparatus 1. The appearance inspection apparatus 1 shown in FIG. 1 represents a preferred embodiment applied to an appearance inspection of a tire T. The appearance inspection apparatus 1 includes a rotation mechanism unit 2 for rotating the tire T, which is a sample to be inspected, a shape acquiring unit 3 for acquiring an external shape of the tire T, a surface condition acquiring unit 4 for acquiring the surface condition of the tire T, and an inspection processing unit 5 for inspecting the shape and the surface condition of the tire T by performing an image processing on the images acquired by the shape acquiring unit 3 and the surface condition acquiring unit 4, respectively. In the present embodiment, the external shape and the surface condition of the tire T are acquired in the form of images, using three types of light having different waveforms from each other. The three types of light having different waveforms from each other are, for example, the three primary colors of light, namely, blue, green, and red. Note that the description hereinbelow is based on the use of blue light, green light, and red light as the three types of light having different waveforms from each other.

The rotation mechanism unit 2 includes a rotating table 21 on which the tire T to be inspected is placed on its side, a motor 22 for rotating the rotating table 21, a rotation angle detecting means 23 for detecting the rotation angle of the rotating table 21, and a motor control means 24 for driving and controlling the motor 22. The rotating table 21, which is formed in a circular disk shape, has a not-shown guide member on its tire mounting surface which positions the tire T concentric therewith. The motor 22, which is connected to the motor control means 24, runs in response to the signals outputted from the motor control means 24. The rotation angle detecting means 23, which is connected to the motor control means 24 and the inspection processing unit 5 to be discussed later, outputs the measured rotation angle of the rotating table 21. The rotation angle detecting means 23 to be used is an encoder, for instance. The motor control means 24 controls the revolution speed and the drive duration of the motor 22 in response to the rotation angle signals outputted from the rotation angle detecting means 23.

The shape acquiring unit 3 includes a first illuminating means 31 for casting a slit light having an intermediate wavelength, of three types of lights having different wavelengths from each other, on a side surface S of a tire under inspection and a first imaging means 32 for receiving reflected light of the light cast on the surface S by the first illuminating means 31. The intermediate wavelength of the different wavelengths of the three types of lights is the wavelength representing a neutral color in the color circle of the three primary colors of light. The colors of light in the color circle are a cycle of red to green to blue to red and on and on. Therefore, red is a neutral color of blue and green, green is a neutral color of red and blue, and blue is a neutral color of green and red. In the present embodiment, green light is employed as a light having an intermediate wavelength of three types, of lights having different wavelengths from each other. Yet, red light or blue light may be used in the place of the green light.

The first illuminating means 31 and the first imaging means 32 are disposed above the tire T, which is placed on the rotating table 21, and secured by not-shown securing means.

The first illuminating means 31 to be employed is a green laser that emits a slit-like green laser beam at the surface S of a tire side. The green laser is so disposed as to illuminate a portion of the surface S such that the slit light runs in a radial direction of the tire from the inner periphery to the outer periphery thereof. Also, the slit light emitted from the green laser is so set as to be directed to the surface S at a predetermined illumination angle. The green laser to be used is a laser light whose central wavelength is about 532 nm, for instance.

Figure 2A:
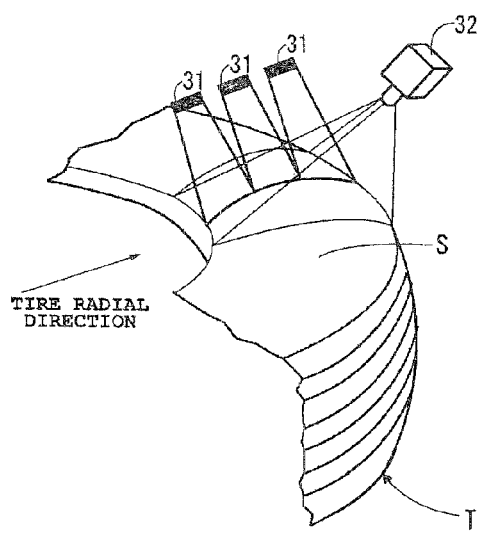
FIG. 2 is illustrations showing other arrangements of first illuminating means.
Figure 2B:
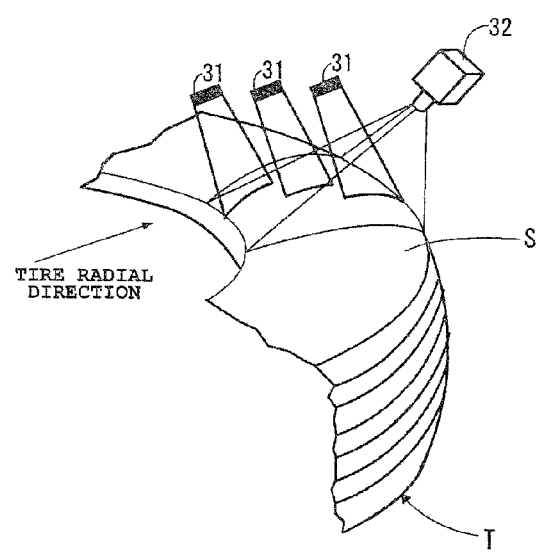

It is to be noted that in cases where the slit light emitted from a single green laser cannot illuminate the whole range from the inner periphery to the outer periphery of the tire because of the large radius of the tire, a plurality of first illuminating means 31 may be arranged in a radial direction of the tire, as shown in FIG. 2A, in such a manner that the green laser light emitted thereby is formed in a straight line and illuminates the whole range from the inner periphery to the outer periphery of the tire. Alternatively, as shown in FIG. 2B, the plurality of first illuminating means 31 may be arranged in a circumferentially staggered manner. In this case, however, care must be taken that there are overlaps between the slit lights emitted from the neighboring first illuminating means 31. Thus, the slit light having an intermediate wavelength may be cast by a plurality of first illuminating means. Hence, the sample surface can be illuminated by a slit light even when the tire under inspection is larger than the width of a single slit light.

It should be noted that the slit-like green laser in this embodiment has an illumination width W set at 50 nm and an effective illumination range set at 90 to 150 mm.

Figure 3:
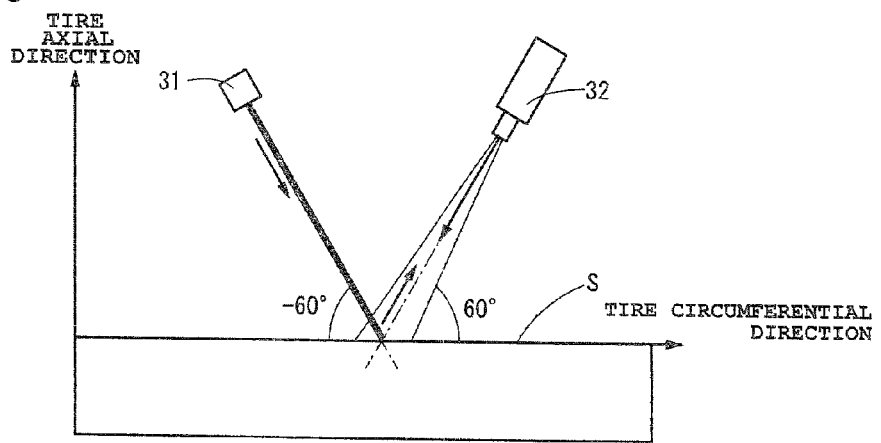
FIG. 3 is an illustration showing the positions of a first illuminating means and a first imaging means relative to the tire side.

FIG. 3 is an illustration showing the positions of a first illuminating means 31 and a first imaging means 32 relative to the surface S of a tire side.

The first imaging means 32, which is, for example, an area camera, is so disposed as to receive the light in mirror reflection of the light cast on the surface S from the green laser. More specifically, as shown in FIG. 3, the first imaging means 32 is so disposed that the light-receiving angle of the optical axis of the first imaging means 32 becomes equal to the illumination angle of the slit light emitted from the green laser. Thus, the first imaging means 32 acquires not only the sectional shape of the tire T at the illuminated portion as sectional shape data but also the reflected luminance data in the sectional shape data by receiving the reflected light of the slit light cast on the surface S from the first illuminating means 31. The sectional shape data and the reflected luminance data are captured from each frame in imaging.

That is, a slit light having an intermediate wavelength is directed at a slant to the surface of a sample under inspection. Hence, the first imaging means 32 can receive the reflected light in a mirror reflection which has the greatest intensity of the slit light reflected on the surface S of the tire being inspected. Accordingly, the shape of the tire surface can be captured with clarity, and a highly accurate inspection can be performed.

The image capturing by the first imaging means 32 is done at predetermined time intervals. And the positional interval is calculated from the rotation angle of the tire T as detected by the rotation angle detecting means 23 and the rotation speed of the tire T.

The first imaging means 32 is disposed such that the direction of the optical axis of the first imaging means 32 for light reception coincides with the direction of the reflected light of the slit light cast by the first illuminating means 31. Thus the reflected light received by the first imaging means 32 is the mirror reflection of the slit light reflected on the surface S. Accordingly, the first imaging means 32 can be set for a maximum luminance of the light received with the result that the shape of the tire at the portion illuminated by the slit light can be captured clearly.

Referring back to FIG. 1, the surface condition acquiring unit 4, which is disposed in a position different from that of the shape acquiring unit 3, includes a second illuminating means 41 for casting two lights having different wavelengths other than the intermediate wavelength, of the three types of lights having different wavelengths from each other, on the surface S and a second imaging means 43 for receiving the reflected light of the lights cast on the surface S by the second illuminating means 41. It should be noted that the second illuminating means 41 employs two lights of blue and green when red light is used by the first illuminating means 31 or two lights of red and green when blue light is used by the first illuminating means 31.

The second illuminating means 41 consists of a red-light illuminator 41A for casting a light of a red-light wavelength and a blue-light illuminator 41B for casting a light of a blue-light wavelength. Those illuminators are disposed a predetermined distance apart from each other in positions on the extension of a tangential line of the tire circumference above one side of the tire and secured by not-shown securing means. The red-light illuminator 41A is an LED illuminator for emitting a red light whose center wavelength is about 660 nm. Also, the blue-light illuminator 41B is an LED illuminator for emitting a blue light whose center wavelength is about 470 nm.

Figure 4A:
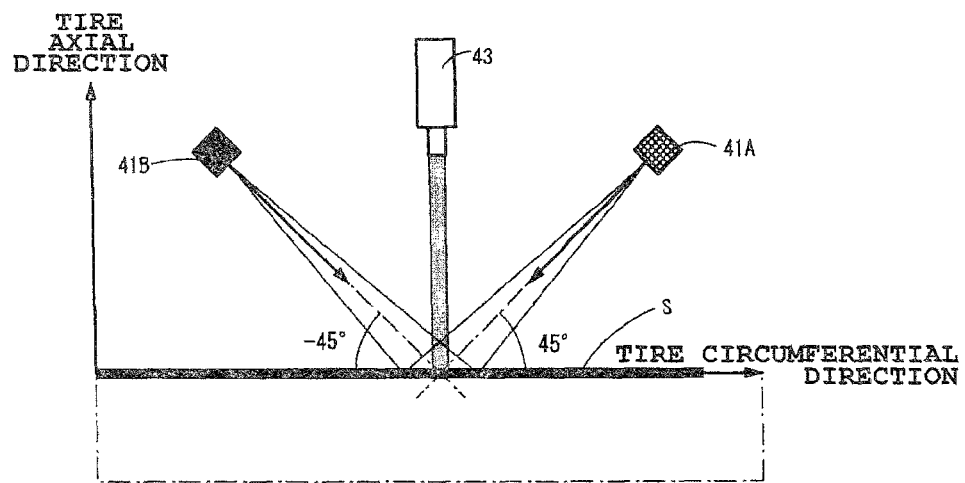
FIG. 4 is diagrams showing the relative positions of a red-light illuminator, a blue-light illuminator, and a second imaging means.
Figure 4B:
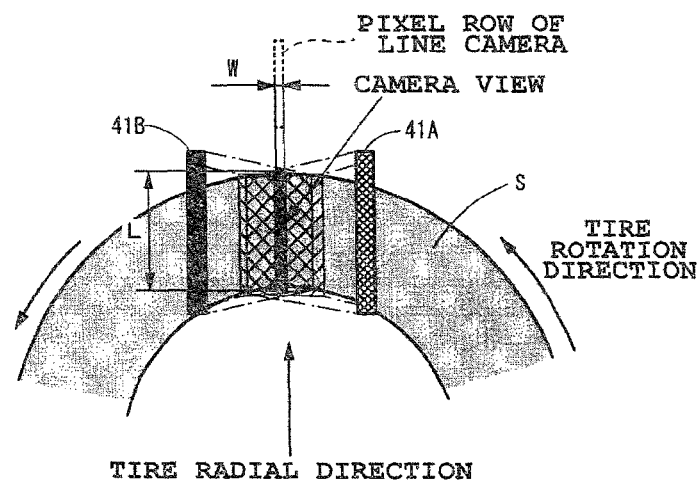

FIGS. 4A and 4B are diagrams showing the relative positions of a red-light illuminator 41A, a blue-light illuminator 41B, and a second imaging means 43.

The red-light illuminator 41A and the blue-light illuminator 41B of the second illuminating means 41 are disposed such that the lights are cast in directions facing each other on a position different from the portion illuminated by the first illuminating means 31 on the surface S of a tire side. The red light and the blue light emitted from the red-light illuminator 41A and the blue-light illuminator 41B illuminate a range from the inner periphery to the outer periphery of the tire in such a manner that they are overlapped with each other on the surface S. The angles of the optical axes of the red light and the blue light cast by the red-light illuminator 41A and the blue-light illuminator 41B, respectively, are set at the same angle, for example, 45 degrees of illumination angle with respect to the surface S. It is to be noted, however, that the illumination angle of the red-light illuminator 41A and the blue-light illuminator 41B is not limited to 45 degrees, but may be set to any same illumination angle within a range of 30 to 70 degrees.

As shown in FIG. 4A, the second imaging means 43 is disposed between the red-light illuminator 41A and the blue-light illuminator 41B above a tire side and secured by a not-shown securing means. The second imaging means 43 receives the reflected light from the portion where the red light and the blue light are overlapped with each other on the surface S. The second imaging means 43 to be employed is a color line camera having a line of light receiving elements. As shown in FIG. 4B, the second imaging means 43, having the light receiving elements arranged in the same direction as a radial direction of the tire, receives the reflected light which is a composition of the red component and the blue component resulting from an overlap of the red light cast by the red-light illuminator 41A and the blue light cast by the blue-light illuminator 41B. In the present embodiment, the second imaging means 43 is so set that the optical axis for light reception is oriented at 90 degrees with respect to the surface S. As such, if the inclinations due to the unevenness or undulation of the surface S cause an imbalance of light reflected from the surface S, then the intensity of a light component as received by the second imaging means 43 will be greater than that of the other.

In the present embodiment, the imaging width W of the second imaging means 43 is 10 μm, the imaging field L is 135 mm, and the imaging is done for every positional shift of about 50 μm (which varies with the diameter of the object to be measured because of a fixed angular speed) in the circumferential direction of the tire T. Note that the shift distance can be calculated from the rotation angle and rotation speed of the tire T as detected by the rotation angle detecting means 23. The images captured by the second imaging means 43 are acquired as surface images consisting of the red component and the blue component of light and outputted to the inspection processing unit 5.

The inspection processing unit 5 is, for instance, a computer that executes the processing for an appearance inspection of the tire T. Therefore the inspection processing unit 5 includes a CPU as arithmetic processing means, an ROM, RAM, and HDD as storage means, and interface as communication means and operates according to a program stored in the storage means. Connected to the inspection processing unit 5 are input means, such as a keyboard and a mouse, and display means, such as a monitor.

Referring back to FIG. 1, the inspection processing unit 5 includes a shape inspecting means 6 for inspecting a 3D shape of the tire T and a surface condition inspecting means 7 for inspecting the surface S. The shape inspecting means 6 includes an image centroid calculating unit 61, an image aligning unit 62, a coordinate transforming unit 63, an image comparison & decision unit 64, and a plane data generating unit 65. And the shape inspecting means 6 inspects the shape and surface condition of the tire T based on the sectional shape data and the surface images.

The image centroid calculating unit 61 calculates the centroid-positions based on the luminance values of a plurality of sectional shape data captured and acquired along the circumferential direction of the tire by the second imaging means 43. To be more specific, the sectional shape data acquired by imaging represents sectional shapes of the surface S of a tire side by assigning color and luminance values to the pixels constituting each of the frames imaged. And then, the image centroid calculating unit 61 calculates centroid positions of the sectional shape data of frames from the positions of the pixels representing the shape and the luminance values of the pixels when the origin is the left above corner of the frame, for instance.

The image aligning unit 62 aligns the sectional shape data such that the centroid positions of all the frames calculated by the image centroid calculating unit 61 are aligned on a straight line. That is, the sectional shape data obtained individually for all the frames are aligned so that their centroid positions coincide with each other. With the sectional shape data aligned by the image aligning unit 62, the processing can be executed as if the sectional shape data has been acquired with the center of the tire T exactly in line with the center of the rotating table 21 even when the data has actually been obtained with the tire T placed eccentrically on the rotating table 21.

The coordinate transforming unit 63 transforms the sectional shape data aligned by the image aligning unit 62 from an orthogonal coordinate system to a cylindrical coordinate system. That is, the sectional shape data acquired by the second imaging means 43 are on the orthogonal coordinates of the frames. Therefore, if 3D tire-like inspection images are to be created from all the sectional shape data, it is necessary to perform a coordinate transformation on all the sectional shape data captured by imaging. Thus, the coordinate transforming unit 63 creates 3D shape data by performing a coordinate transformation on all the sectional shape data based on the captured rotation angles.

The image comparison & decision unit 64 compares the 3D shape data against the 3D master data of the tire T under inspection, which has been stored in advance in the storage unit of the inspection processing unit 5, and detects the difference of the 3D shape data from the master data. Thereupon, the image comparison & decision unit 64 determines no shape anomaly when the difference between the master data and the 3D shape data is smaller than the threshold or shape anomaly when the difference is greater than the threshold.

The plane data generating unit 65 generates plane data, excluding height information, from the sectional shape data aligned by the image aligning unit 62. The plane data is reflected luminance data of individual frames aligned in a straight line after extracting the reflected luminance data only of the aligned sectional shape data. In other words, the plane data is green component images of the surface S of a tire side acquired using the green component light. Hereinbelow, the plane data will be referred to as green component images.

The surface condition inspecting means 7 includes a color component separating means 16, an extraneous color defect detecting means 17, an unevenness defect detecting means 18, and a gloss defect detecting means 19.

Figure 5:
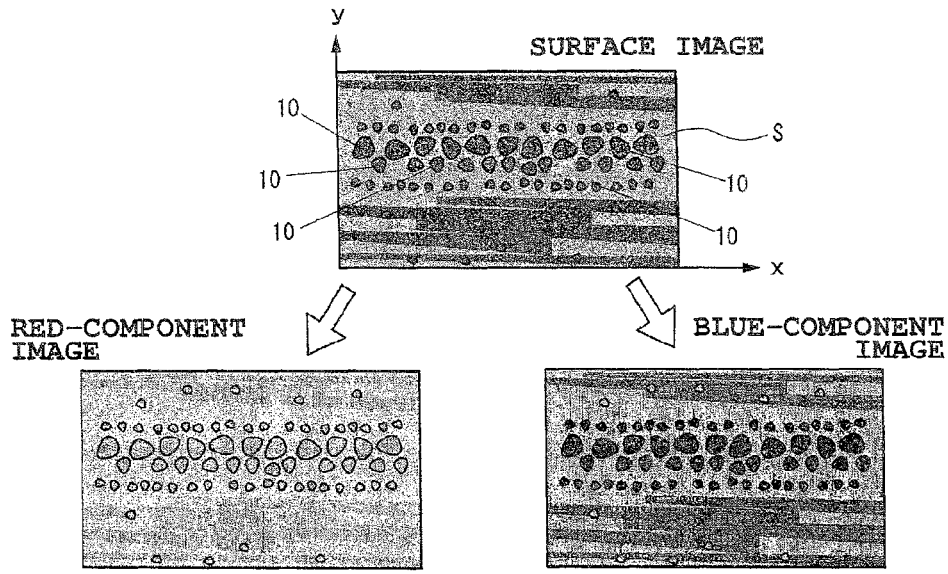
FIG. 5 is conceptual representations showing separation of a surface image into a red-component image and a blue-component image.

FIG. 5 is conceptual representations showing separation of a surface image into a red component image and a blue component image. Note that the reference numeral 10 in the figure represents indents to be detected in a subsequent detection process.

The color component separating means 16, as shown in FIG. 5, separates a 2D surface image of the surface S captured by the second imaging means 43 into a red component and a blue component, thereby creating two images of a red-component image and a blue-component image.

The extraneous color defect detecting means 17 includes a luminance component normalizing unit 71, a color image synthesizing unit 72, an extraneous color decision unit 73, and an extraneous color storage unit 74.

Figure 6A:
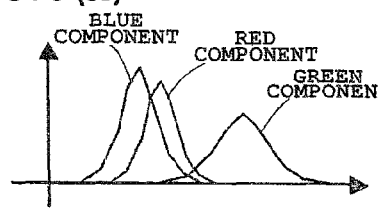
FIG. 6 is graphs showing a standard deviation a of the luminance values of green-component image, red-component image, and blue-component image.
Figure 6B:
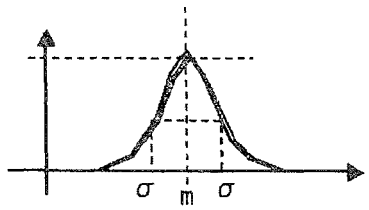

FIG. 6A is a graph showing the standard deviations σ of the luminance values of a green-component image, a red-component image, and a blue-component image. FIG. 6B shows the luminance values of the green-component image, red-component image, and blue-component image lined up by scaling the luminance values based on the standard deviations σ.

The luminance component normalizing unit 71 normalizes the green-component image captured by the first imaging means 32 and the red-component image and the blue-component image created by the color component separating means 16, respectively. More specifically, the luminance component normalizing unit 71 first performs a position adjustment of the green-component image, which is positionally dislocated due to the difference in imaging start position, to the red-component image and blue-component image.

Then the luminance component normalizing unit 71 calculates the means m and standard deviations σ of the respective color component images constituting the green-component image, the red-component image, and the blue-component image, as shown in FIG. 6A, and normalize the green-component image, the red-component image, and the blue-component image by lining them up with reference to the means m and standard deviations σ.

That is, since the green-component image, the red-component image, and the blue-component image have their luminances differing from each other, the values of their means m and standard deviations σ also differ from one to the other. Therefore, the luminances of the green-component image, the red-component image, and the blue-component image can be evened up by shifting and scaling the pixel values in such a manner as to equalize the means m and standard deviations σ of the respective color component images. As a result, a clear color image without a bias in color components can be generated when the green-component image, the red-component image, and the blue-component image are synthesized.

The color image synthesizing unit 72 synthesizes the green-component image, red-component image, and blue-component image normalized by the luminance component normalizing unit 71 into a 2D color image.

The extraneous color decision unit 73 decides on the presence or absence of extraneous color by comparing the color image synthesized by the color image synthesizing unit 72 against a predetermined threshold. More specifically, the extraneous color decision unit 73 performs an image processing filtering calculation to extract the amount of defect characteristic from the color image and determines the presence of extraneous color when the amount of defect characteristic is larger than the threshold and the absence of extraneous color when it is smaller than the threshold. It is to be noted that the extraneous color meant here refers to the "shine" of the mold release agent having adhered to the surface S of the tire T during the cure-molding of the tire T or the "change in color tone" of the rubber due to the heating during the cure-molding process, for instance.

Also, as another method for determining an extraneous color by the extraneous color decision unit 73, the presence of an extraneous color may be determined when the gradient between the luminance values of any neighboring pixels of the pixels constituting a color image is greater than a threshold and the absence of it when the gradient is smaller than the threshold.

The extraneous color storage unit 74 stores the position and size of the extraneous color detected as an extraneous color by the extraneous color decision unit 73.

The unevenness defect detecting means 18 includes a luminance distribution waveform calculating unit 81, a peak interval calculating unit 82, a peak interval decision unit 83, a surface inclination angle calculating unit 84, an unevenness decision unit 85, and an unevenness storage unit 86. And the unevenness defect detecting means 18 detects the adhesion of minute foreign matter on the surface S, the surface roughness or minute flaws caused during the molding, and the like.

Figure 7:
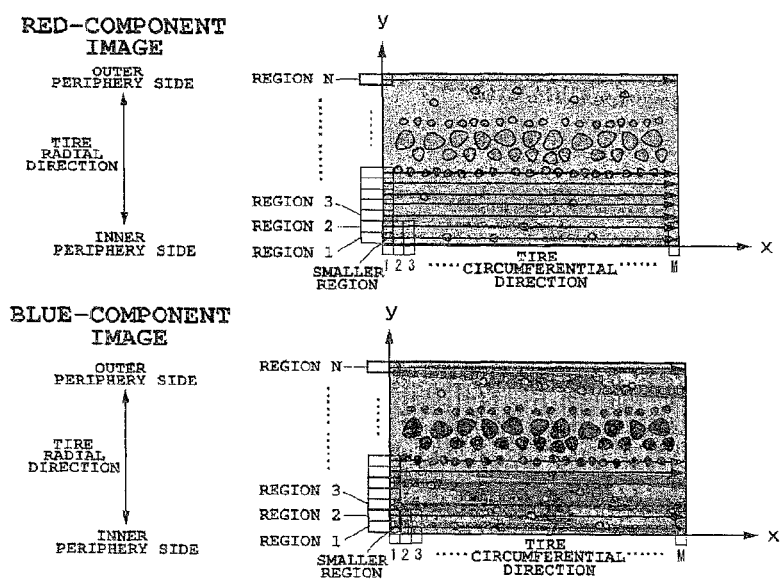
FIG. 7 is conceptual representations showing division of a red-component image and a blue-component image into smaller regions.

FIG. 7 is conceptual representations showing division of a red-component image and a blue-component image into smaller regions.

The luminance distribution waveform calculating unit 81 calculates a mean and standard deviation of the pixel values within a range under inspection of each of the red-component images and blue-component images by handling the luminance distribution contained in each of the red-component images and blue-component images as approximating a normal distribution.

The peak interval calculating unit 82 detects a red peak in the luminance distribution waveform of each of the smaller regions of a red-component image and a blue peak of each of the smaller regions of a blue-component image and calculates the interval between the red peak and the blue peak in each of the smaller regions in the corresponding positions in the red-component image and the blue-component image.

The peak interval decision unit 83 compares the peak interval in each of the smaller regions calculated by the peak interval calculating unit 82 against a predetermined threshold and decides on the absence of surface unevenness when the peak interval is below the threshold and on the presence of anomaly when the peak interval is at or above the threshold.

That is, when the interval between the peak of the red component and the peak of the blue component is smaller than the threshold, the peak interval decision unit 83 decides on the absence of minute flaws, unevenness, and undulation on the surface S. And when the interval between the peak of the red component and the peak of the blue component is equal to or larger than the threshold, the peak interval decision unit 83 decides on the presence of minute flaws, unevenness, and undulation on the surface S because in this case one of the color components may be blocked or diffused by the flaw or unevenness in the portion illuminated by the light.

As described above, the present invention realizes the detection of minute flaws, unevenness, and undulation on the surface S.

Figure 8A:
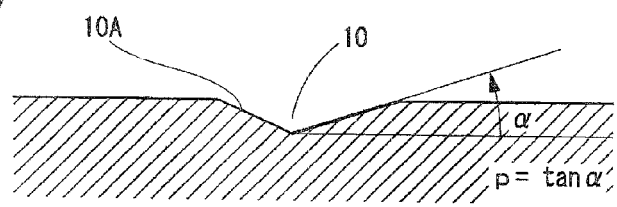
FIG. 8 is conceptual diagrams for calculation of a surface inclination angle.

FIG. 8A is a schematic illustration showing an indent in the surface S of a tire side. FIG. 8A is a conceptual representation for the calculation of the surface inclination angle α of the indent in the surface S of a tire side. It should be noted here that the indent 10, if it is deep and wide, can be detected in the shape inspection. The surface inclination angle calculating unit 84 calculates the surface inclination angle α, which represents the degree of inclination in the unevenness of the surface S when the presence of anomaly in the peak interval is determined by the peak interval decision unit 83.

The surface inclination angle α is calculated as follows:

Let p denote the inclination in the circumferential direction of the tire and q the inclination in the radial direction of the tire at point P (x, y, z) on the surface S, then the p and q can be expressed by the following equations. Note that the subscript B stands for blue light and the subscript R red light. For example, $p_B$ represents the blue component of light along the inclination p, and $P_R$ the red component of light along the inclination p. Similarly, $q_B$ represents the blue component of light along the inclination q, and $q_R$ the red component of light along the inclination q.

$$p = \frac{\partial z}{\partial x}, \quad q = \frac{\partial z}{\partial y} \qquad \text{[Equation 1]}$$

Also, the vector n normal to the surface S under inspection can be expressed by the following equation using the above p and $$n = \frac{1}{\sqrt{p^2 + q^2 + 1}}(-p, -q, 1) \qquad \text{[Equation 2]}$$

On the other hand, the incident light vector $S_R$ of the red light cast by the red-light illuminator 41A and the incident light vector $S_B$ of the blue light cast by the blue-light illuminator 41B can be expressed by the following equation where $I_R$ is the intensity of the red light and $I_B$ is the intensity of the blue light.

$$S_R = \frac{I_R}{\sqrt{p_R^2 + q_R^2 + 1}}(-p_R, -q_R, 1) \qquad \text{[Equation 3]}$$

$$S_B = \frac{I_R}{\sqrt{p_B^2 + q_B^2 + 1}}(-p_R, -q_B, 1)$$

Also, as shown by the following equation, the intensity $E_R$ of the red light received by the second imaging means 43 is an orthogonal projection of the incident light vector $S_R$ to the normal vector n multiplied by the reflectance ρ of the tire T under inspection, and the intensity $E_B$ of the blue light received by the second imaging means 43 is an orthogonal projection of the incident light vector SE to the normal vector n multiplied by the reflectance ρ.

$$E_R = \rho(S_R \cdot n) = \qquad \text{[Equation 4]}$$
$$\rho I_R \frac{1}{\sqrt{p^2 + q^2 + 1}} \frac{1}{\sqrt{p_R^2 + q_R^2 + 1}}(pp_R + qq_R + 1)$$

$$E_B = \rho(S_B \cdot n) = \rho I_B \frac{1}{\sqrt{p^2 + q^2 + 1}}$$
$$\frac{1}{\sqrt{p_B^2 + q_B^2 + 1}}(pp_B + qq_B + 1)$$

Figure 8B:
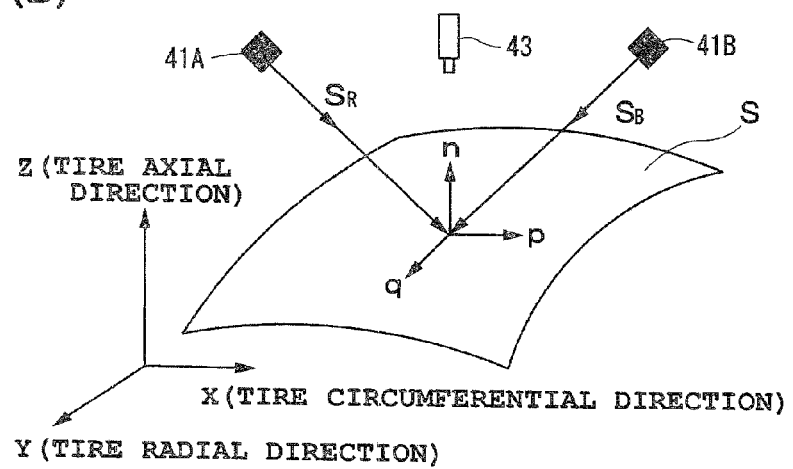

Accordingly, the inclination p in the circumferential direction of the tire on the surface S can be calculated by eliminating the inclination q in the radial direction of the tire from the equation of the intensity $E_R$ of the red light and the equation of the intensity $E_B$ of the blue light. It is to be noted that the inclination p, as shown in FIG. 8B, is in a relationship of p=tan α with the surface inclination angle α, which is the degree of inclination of an inner surface of the unevenness 10A (see FIG. 8A) in an x-z cross section of the tire side. Hence, the surface inclination angle α can be expressed by the following equation.

$$\alpha = \tan^{-1} p = \tan^{-1} \frac{\beta}{p_R - \beta \cdot p_B} \qquad \text{[Equation 5]}$$

where $$\beta = \frac{\sqrt{p_R^2 + 1}}{\sqrt{p_B^2 + 1}} \cdot \frac{E_R}{E_B} \cdot \frac{I_B}{I_R}$$

Thus, the surface inclination angle calculating unit 84 calculates the surface inclination angle α using the equation 5.

The unevenness decision unit 85 compares the surface inclination angle α against a predetermined threshold and determines whether the cause of the peak interval being at or above the threshold is attributable to surface unevenness or not. That is, the unevenness decision unit 85 decides on the presence of abnormal unevenness when the surface inclination angle α is equal to or greater than the threshold and on the absence of surface unevenness when the surface inclination angle α is smaller than the threshold.

The unevenness storage unit 86 stores the position and the surface inclination angle α of the tire T when the presence of surface unevenness is decided by the unevenness decision unit 85 or the position of the tire T when the absence of surface unevenness is decided by the unevenness decision unit 85. Note that the position of the tire T when the absence of surface unevenness is decided by the unevenness decision unit 85 is stored for use as an indicator for a decision making in a subsequent process.

The gloss defect detecting means 19 compares the image of a position, of which the surface inclination angle α is detected by the surface inclination angle calculating unit 84 and yet the absence of surface unevenness is decided by the unevenness decision unit 85, against the color image of the corresponding position and determines the absence of anomaly if no anomaly of the position is decided by the extraneous color defect detecting means 17, that is, there is no anomaly in the color image or the presence of a gloss defect if any anomaly is decided by the extraneous color defect detecting means 17.

Hereinbelow, a description is given of the processing for an appearance inspection of a tire T by an appearance inspection apparatus.

First a tire T to be inspected is placed on a rotating table 21. At the same time, a shape acquiring unit 3, which consists of a first illuminating means 31 and a first imaging means 32, is set directly above a side of the tire T, and a surface condition acquiring unit 4, which consists of a red-light illuminator 41A, a blue-light illuminator 41B, and a second imaging means 43, in a position dislocated by a predetermined angle in the circumferential direction from the shape acquiring unit 3. Then the tire T is rotated at a predetermined rotation speed by rotating the rotating table 21 by controlling the drive of a motor 22.

Next, a slit-like green laser light is cast on the surface S of the tire T by the first illuminating means 31, and the portion illuminated by the slit light is captured by the first imaging means 32. At the same time, a red light and a blue light are cast on the surface S by the red-light illuminator 41A and the blue-light illuminator 41B in such a manner as to overlap them with each other, and the portion illuminated by the overlapped red light and blue light is captured by the second imaging means 43.

And the sectional shape data and surface images of the tire side are acquired for one rotation of the tire.

Next, after the surface images and sectional shape data for one rotation of the tire are inputted to the inspection processing unit 5, an inspection processing is started by the inspection processing unit 5.

Figure 9:
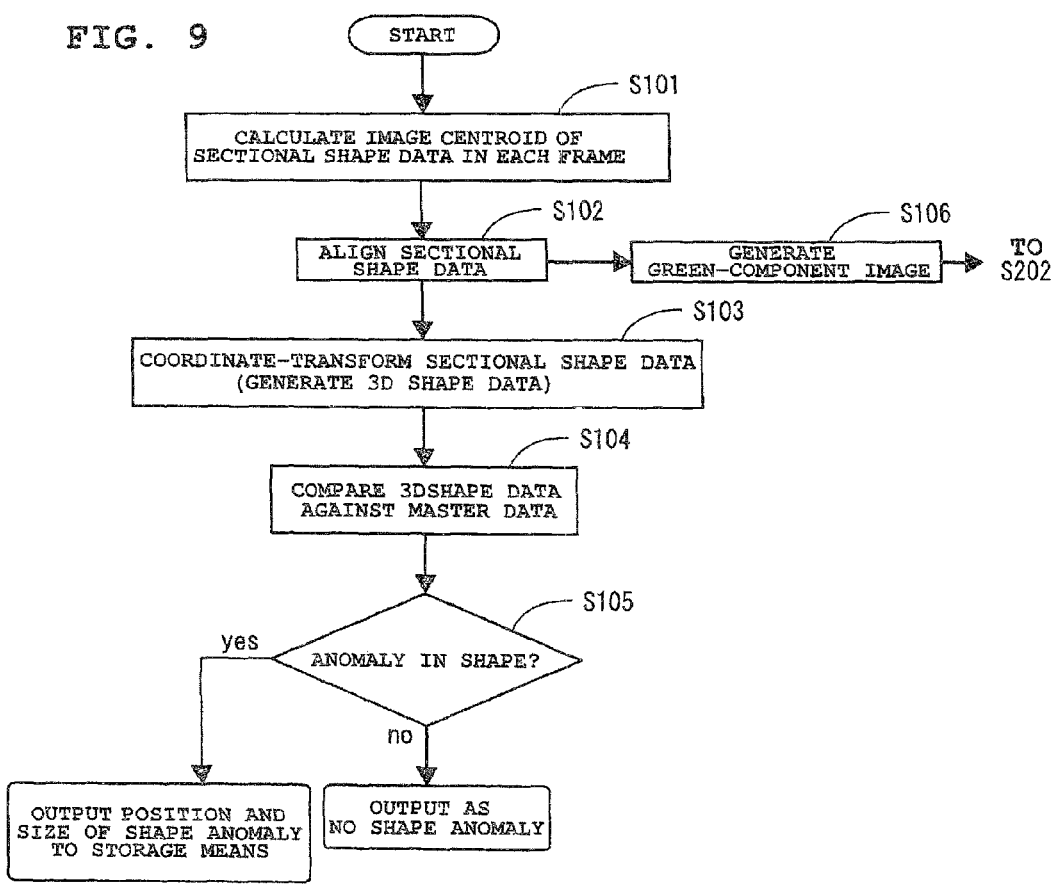
FIG. 9 is a flowchart showing a processing by an inspection processing unit.

FIGS. 9 and 10 are flowcharts of inspection processing by the inspection processing unit 5. Hereinbelow, a description is given of the processing of an appearance inspection of the tire. T by the inspection processing unit 5 with reference to FIGS. 9 and 10.

First the inspection processing unit 5 calculates the image centroids of a plurality of sectional shape data acquired by the image centroid calculating unit 61 (S101). Then the image aligning unit 62 aligns the sectional shape data such that the image centroids of all the frames are placed in the same position (S102). Then the coordinate transforming unit 63 performs a coordinate transformation transforming the sectional shape data into 3D shape data of tire shape (S103). Also, the plane data generating unit 65 generates a green-component image of the surface S by extracting the plane data of luminance information only by excluding the height information contained in each of the aligned sectional shape data (S106).

Next, the image comparison & decision unit 64 compares the 3D shape data against the master data and decides on the presence or absence of shape anomaly (S104). To be more specific, the 3D coordinates constituting the 3D shape data are compared with the 3D coordinates of the master data, the difference in each coordinate position is calculated, and the presence of shape anomaly is decided when the difference is at or above a threshold or the absence of shape anomaly is decided when the difference is below the threshold (S105).

Next, an inspection of the surface S of the tire T is performed by the surface condition inspecting means 7.

First the surface condition inspecting means 7 has a surface image separated into a red-component image and a blue-component image by the color component separating means 16 (S201). Then the extraneous color defect detecting means 17 makes an inspection for extraneous color on the surface S. More specifically, the extraneous color defect detecting means 17 normalizes the luminance components contained in the green-component image outputted in S106 and in the red-component image and blue-component image separated in S201 (S202). Normalization of the luminance components in this embodiment is adjustment of the luminances of the green-component image, red-component image, and blue-component image to approximately the same level because the information concerning the luminance values contained in the green-component image, red-component image, and blue-component image varies greatly with one another. Also, the luminance component normalizing unit 71 performs not only the normalization of the luminance components in the green-component image, red-component image, and blue-component image, but also the position adjustment of the green-component image, red-component image, and blue-component image (S203).

Next, the color image synthesizing unit 72 synthesizes the green-component image, red-component image, and blue-component image into a color image upon the normalization of the luminance components (S204). Then the color image is subjected to an image processing filtering calculation by the extraneous color decision unit 73 as in the steps S205 through S212, for instance, to determine the presence or absence of any extraneous color. With the decision on the presence or absence of extraneous color completed, the procedure goes to S301. If the processing for all the smaller regions is not completed, then the procedure does to S122 and the processing from S208 to S212 is repeated.

Next, the unevenness defect detecting means 18 further detects minute unevenness on the surface S which cannot be detected by the shape detecting means 6. First the luminance distribution waveforms for the red-component image and the blue-component image, respectively, are calculated by the luminance distribution waveform calculating unit 81. More specifically, the red-component image and the blue-component image are divided into smaller regions of the same size as those divided by the extraneous color decision unit 73 (S301). A luminance mean is calculated for each of the smaller regions (k=1). Then the luminance distribution waveforms of the smaller regions of the red-component image and the blue-component image, respectively, are calculated (S303). Then the red peaks and the blue peaks in the red-component image and the blue-component image, respectively, are detected (S304). Then the peak intervals between the red peaks and the blue peaks are calculated (S305) Then a decision is made as to whether the peak interval is at or above the threshold, and the processing goes to S307 if it is at or above the threshold or goes to S311 if it is smaller than the threshold (S306). At S307, the surface inclination angle is calculated (S307). Then a decision is made as to whether the calculated surface inclination angle is at or above the threshold, and the processing goes to S309 if the surface inclination angle is at or above the threshold or goes to S311 if it is smaller than the threshold (S308). By going to S309, the position of surface unevenness and the surface inclination angle of the anomaly in surface inclination angle are recorded in the unevenness storage unit 86 which is the storage means (S309). Next, a decision is made as to whether the processing for all the smaller regions is completed or not (S310). And the processing goes to S401 if the processing for all the smaller regions is completed or goes to S311 if the processing for all the smaller regions is not completed and the procedure from S303 to S310 is repeated.

And when the absence of surface unevenness is determined by the unevenness defect detecting means 18, the absence of surface unevenness is outputted to the unevenness storage unit 86. Or when the presence of surface unevenness is determined, the inclination angle α on the surface S of a tire side is calculated by the surface inclination angle calculating unit 84. Then the calculated surface inclination angle α is compared with the threshold. And when the surface inclination angle α is smaller than the threshold, no anomaly is determined, and when the surface inclination angle α is at or above the threshold, an anomaly is determined. It is to be noted that when a surface inclination angle α is calculated, the surface inclination angle α is stored in the unevenness storage unit 86 irrespective of the presence or absence of anomaly in the surface inclination angle α.

Next, the gloss defect detecting means 19 detects a gloss defect by comparing the position of surface unevenness recorded in the unevenness storage unit 86 against the position stored in the extraneous color storage unit 74 corresponding to the position of which no anomaly in the surface inclination angle α is determined (S401). In other words, an anomaly of gloss defect is determined for the position where no anomaly in the surface inclination angle α is determined but the presence of extraneous color is determined. And no anomaly of gloss defect is determined for the position where no anomaly in the surface inclination angle α is determined and also the absence of extraneous color is determined. The case like this suggests that an inspection error has occurred. After all these steps, the processing by the inspection processing unit 5 comes to an end.

As thus far described, a green-component image is generated by extracting an image of the tire surface S from the shape data acquired by casting a green slit-like laser light. Now color tones on the tire surface S can be obtained with accuracy through generating a color image by synthesizing the green-component image with the red-component image and the blue-component image. Also, the "change in color tone" and "shine" on the tire surface S can be determined with precision by subjecting the color image to an image processing. Therefore, the accuracy of inspection of the shape and surface condition of the tire T can be improved.

The preferred embodiments so far have been described on the assumption that a tire is the sample under inspection. However, they are not limited to the tire only, but can be applied to the inspection of members constituting a tire and other molded articles such as hoses and pipes.

Also, those preferred embodiments have been described on the assumption that the red-light illuminator 41A and the blue-light illuminator 41B of the second illuminating means 41 are LED illuminators. However, they are not limited to LED illuminators, but any light sources casting diffusion light may be employed.

DESCRIPTION OF REFERENCE NUMERALS 1 appearance inspection apparatus
5 inspection processing unit
6 shape inspecting means
7 surface condition inspecting means
16 color component separating means
17 extraneous color defect inspecting means
18 unevenness defect detecting means
19 gloss defect detecting means
31 first illuminating means
32 first imaging means
41 second illuminating means
43 second imaging means
61 image centroid calculating unit
62 image aligning unit
63 coordinate transforming unit
64 image comparison & decision unit
65 plane data generating unit
71 luminance component normalizing unit
72 color image synthesizing unit
73 extraneous color decision unit
74 extraneous color storage unit
81 luminance distribution waveform calculating unit
82 peak interval calculating unit
83 peak interval decision unit
84 surface inclination angle calculating unit
85 unevenness decision unit
86 unevenness storage unit

The invention claimed is:

1. An appearance inspection apparatus comprising:
a first illuminating unit configured to cast a slit light on a surface of a sample under inspection, the slit light being green wavelength light;
a first camera configured to acquire reflected luminance data on the surface of the sample by receiving reflected light of the slit light;
a second illuminating unit configured to cast two lights of blue wavelength and red wavelength on a position other than a position illuminated by the slit light on the sample surface from two different directions so as to overlap the two lights with each other;
a second camera configured to acquire surface data on the sample surface by receiving reflected light from the position where the two lights are overlapped with each other;
a shaping inspection unit configured to acquire green component images from the reflected luminance data;
a color component separating unit configured to acquire red component images and blue component images from the surface data;
an unevenness defect detecting unit configured to detect presence or absence of surface unevenness from a ratio between intensities of the two lights contained in the surface data;
an extraneous color defect detecting unit configured to detect changes in color tone on the sample surface by normalizing the green component images, the red component images and the blue component images and synthesizing the normalized green component images, the red component images and the blue component images into a 2D color image; and
a gloss defect detecting unit configured to detect gloss on the sample surface based on the presence or absence of surface unevenness and the changes in color tone of the 2D color image.

2. The appearance inspection apparatus according to claim 1, wherein the slit light is cast at a slant on the sample surface.

3. The appearance inspection apparatus according to claim 2, wherein the slit light is formed by a plurality of first illuminating units.

4. The appearance inspection apparatus according to claim 1, wherein the slit light is formed by a plurality of first illuminating units.

5. An appearance inspection method comprising the steps of:
casting a slit light on a surface of a sample under inspection with a first illuminating unit, the slit light being green wavelength light;
acquiring reflected luminance data on the surface of the sample by receiving reflected light of the slit light with a first camera;
casting two lights of blue wavelength and red wavelength on a position other than a position illuminated by the slit light on the sample surface with a second illuminating unit from two different directions so as to overlap the two lights with each other;
acquiring surface data on the sample surface by receiving reflected light from the position where the two lights are overlapped with each other with a second camera;
acquiring green component images from the reflected luminance data with a shaping inspection unit;
acquiring red component images and blue component images from the surface data with a color component separating unit;
detecting presence or absence of surface unevenness from a ratio between intensities of the two lights contained in the surface data with an unevenness defect detecting unit;
detecting changes in color tone on the sample surface by normalizing the green component images, the red component images and the blue component images and synthesizing the normalized green component images, the red component images and the blue component images into a 2D color image with an extraneous color defect detecting unit; and
detecting gloss on the sample surface based on the presence or absence of surface unevenness and the changes in color tone of the 2D color image with a gloss defect detecting unit.

* * * * *